United States Patent
Chu et al.

[11] Patent Number: 6,030,834
[45] Date of Patent: Feb. 29, 2000

[54] HUMAN IKK-BETA DNA CONSTRUCTS AND CELLS

[75] Inventors: Keting Chu, Burlingame; David Pot, San Francisco, both of Calif.

[73] Assignee: Chiron Corporation, Emeryville, Calif.

[21] Appl. No.: 09/215,131

[22] Filed: Dec. 18, 1998

Related U.S. Application Data

[60] Provisional application No. 60/068,954, Dec. 30, 1997.

[51] Int. Cl.[7] .......................... C12N 15/85; C12N 15/54; C12N 15/63; C07H 21/04
[52] U.S. Cl. ...................... 435/325; 435/194; 435/253.2; 435/254.2; 435/320.1; 435/455; 435/471; 536/23.1; 536/23.2; 536/23.5
[58] Field of Search ................................ 435/194, 252.3, 435/325, 6; 536/23.1, 24.31, 24.33, 23.5

[56] References Cited

U.S. PATENT DOCUMENTS 5,851,812   12/1998   Goeddel et al. ......................... 435/194

FOREIGN PATENT DOCUMENTS

| | | |
|---|---|---|
| 97/35014 | 9/1997 | WIPO . |
| 98/08955 | 3/1998 | WIPO . |
| 98/37228 | 8/1998 | WIPO . |

OTHER PUBLICATIONS

Woronicz J.D. et al. "I(kappa) B kinase–(beta): NF–(kappa)B activation and complex formation with I(kappa)B kinase–(alpha) and NIK" Science, vol. 278 Oct. 31, 1997 pp. 866–869.

Mercurio F. et al. "IKK–1 and IKK–2: cytokine–activated IkappaB kinases essential for NF –kappaB activation" Science, vol. 278, Oct. 31, 1997 pp. 860–866.

Maniatis T. "Catalysis by a Multiprotein I(KAPPA)B Kinase Complex" Science, vol. 278, Oct. 31, 1997, pp. 818–819.

Nakano H. et al. "Differential regulation of IkappaB kinase alpha and beta by two upstream kinases, NF–kappaB–inducing kinase and mitogen–activated protein kinase / ERK kinase—1" Proceedings of the National Academy of Sciences of the United States of America, vol. 95, No. 7, Mar. 31, 1998 pp. 3537–3542.

*Primary Examiner*—John L. LeGuyader
*Assistant Examiner*—Janet Epps
*Attorney, Agent, or Firm*—Lisa M. Hemmendinger; Kimberlin L. Morley; Robert P. Blackburn

[57] ABSTRACT

A novel kinase has been identified which phosphorylates IκB. Reagents which inhibit this kinase can be used as therapeutic tools to inhibit inflammation. The kinase can also be used as a target for drug screening to identify anti-inflammatory compounds.

15 Claims, No Drawings

SEQUENCE LISTING

```
<160> NUMBER OF SEQ ID NOS: 3

<210> SEQ ID NO 1
<211> LENGTH: 3966
<212> TYPE: DNA
<213> ORGANISM: human

<400> SEQUENCE: 1
atgagctggt caccttccct gacaacgcag acatgtgggg cctgggaaat gaaagagcgc      60
cttgggacag ggggatttgg aaatgtcatc cgatggcaca atcaggaaac aggtgagcag     120
attgccatca agcagtgccg gcaggagctc agcccccgga accgagagcg gtggtgcctg     180
gagatccaga tcatgagaag gctgacccac cccaatgtgg tggctgcccg agatgtccct     240
gaggggatgc agaacttggc gcccaatgac ctgcccctgc tggccatgga gtactgccaa     300
ggaggagatc tccggaagta cctgaaccag tttgagaact gctgtggtct gcgggaaggt     360
gccatcctca ccttgctgag tgacattgcc tctgcgctta gataccttca tgaaaacaga     420
atcatccatc gggatctaaa gccagaaaac atcgtcctgc agcaaggaga acagaggtta     480
atacacaaaa ttattgacct aggatatgcc aaggagctgg atcagggcag tctttgcaca     540
tcattcgtgg ggaccctgca gtacctggcc ccagagctac tggagcagca gaagtacaca     600
gtgaccgtcg actactggag cttcggcacc ctggcctttg agtgcatcac gggcttccgg     660
cccttcctcc ccaactggca gcccgtgcag tggcattcaa aagtgcggca gaagagtgag     720
gtggacattg ttgttagcga agacttgaat ggaacggtga agttttcaag ctctttaccc    780
```

```
tacccccaata atcttaacag tgtcctggct gagcgactgg agaagtggct gcaactgatg    840
ctgatgtggc acccccgaca gaggggcacg gatcccacgt atgggcccaa tggctgcttc    900
aaggccctgg atgacatctt aaacttaaag ctggttcata tcttgaacat ggtcacgggc    960
accatccaca cctaccctgt gacagaggat gagagtctgc agagcttgaa ggccagaatc   1020
caacaggaca cgggcatccc agaggaggac caggagctgc tgcaggaagc gggcctggcg   1080
ttgatccccg ataagcctgc cactcagtgt atttcagacg gcaagttaaa tgagggccac   1140
acattggaca tggatcttgt ttttctcttt gacaacagta aaatcaccta tgagactcag   1200
atctccccac ggccccaacc tgaaagtgtc agctgtatcc ttcaagagcc caagaggaat   1260
ctcgccttct tccagctgag gaaggtgtgg ggccaggtct ggcacagcat ccagaccctg   1320
aaggaagatt gcaaccggct gcagcaggga cagcgagccg ccatgatgaa tctcctccga   1380
aacaacagct gcctctccaa aatgaagaat tccatggctt ccatgtctca gcagctcaag   1440
gccaagttgg atttcttcaa aaccagcatc cagattgacc tggagaagta cagcgagcaa   1500
accgagtttg ggatcacatc agataaactg ctgctggcct ggagggaaat ggagcaggct   1560
gtggagctct gtgggcggga aacgaagtg aaactcctgg tagaacggat gatggctctg   1620
cagaccgaca ttgtggactt acagaggagc cccatgggcc ggaagcaggg gggaacgctg   1680
gacgacctag aggagcaagc aagggagctg tacaggagac taagggaaaa acctcgagac   1740
cagcgaactg agggtgacag tcaggaaatg gtacggctgc tgcttcaggc aattcagagc   1800
ttcgagaaga agtgcgagt gatctatacg cagctcagta aaactgtggt ttgcaagcag   1860
aaggcgctgg aactgttgcc caaggtggaa gaggtggtga gcttaatgaa tgaggatgag   1920
aagactgttg tccggctgca ggagaagcgg cagaaggagc tctggaatct cctgaagatt   1980
gcttgtagca aggtccgtgg tcctgtcagt ggaagcccgg atagcatgaa tgcctctcga   2040
cttagccagc ctgggcagct gatgtctcag ccctccacgg cctccaacag cttacctgag   2100
ccagccaaga agagtgaaga actggtggct gaagcacata acctctgcac cctgctagaa   2160
aatgccatac aggacactgt gagggaacaa gaccagagtt tcacggccct agactggagc   2220
tggttacaga cggaagaaga agagcacagc tgcctggagc aggcctcatg atgtgggggg   2280
actcgacccc ctgacatggg gcagcccata gcaggccttg tgcggtgggg ggactcgacc   2340
ccctgacatg gggctgcctg gagcaggccg cgtgacgtgg ggctgcctgg ccgcggctct   2400
cacatggtgg ttcctgctgc actgatggcc cagggtctc tggtatccag atggagctct   2460
cgcttcctca gcagctgtga ctttcaccca ggacccagga cgcagccctc cgtgggcact   2520
gccggcgcct tgtctgcaca ctggaggtcc tccattacag aggcccagcg cacatcgctg   2580
gccccacaaa cgttcagggg tacagccatg gcagctcctt cctctgccgt gagaaaagtg   2640
cttggagtac ggtttgccac acacgtgact ggacagtgtc caattcaaat ctttcagggc   2700
agagtccgag cagcgcttgg tgacagcctg tcctctcctg ctctccaaag gccctgctcc   2760
ctgtcctctc tcactttaca gcttgtgttt cttctggatt cagcttctcc taaacagaca   2820
gtttaattat agttgcggcc tggccccatc ctcacttcct cttttttattt cactgctgct   2880 aaaattgtgt ttttacctac tactttggtg gttgtcctct tttcggcaaa gttggagcga   2940
gtgccaagct ctccatctgt ggtcctttct gccaagagcg actcatagta accaggatgg   3000
gagagcagct gccttattct gaatcccaaa aattacttgg gggtgattgt cacagaggag   3060
ggacagaaag ggtatctgct gaccaccagc ctgcctaccc atgcccatgt ctccattcct   3120
```

-continued

```
gctcaagcgt gtgtgctggg ccggggagtc cctgtctctc acagcatcta gcagtattat    3180
taaatggatt cattttaaaa atagctccta tattttgtaa catgtctcaa acactcatac    3240
tgggttccac aatccactgt tagaatacct atggttaggg cttctgaact aaaataatgg    3300
aaaattttaa caatttgtat agtgcctgga tcattactag tgccataacc ctgcttcttc    3360
aacatttcac agaacttctc ttttatataa aggcaagagc acaaaatgag ttcagatgat    3420
cacaaacagg tgagttttgt tggagaagaa agttggagta ggagactttc acaagtggtt    3480
tccatggaga tagaatgaag cattctgtgg tcaagtaagt ttagggagct attcatgttt    3540
cacttgcttt gtggagattc acactatgca ctgggaaagt atctgaaaag tcttataata    3600
aagaaacagg cttaactttg tgtaagaaca ctgtttatca atgtcatttg ctatagaaa    3660 cattttctcc tgctgattgt gtgtgtgaaa catgtattaa cattccaatg aactagcatt    3720
taataaagca caattttgga aaccctggta aatgacagtg ggaaataaca cccgaaaggc    3780
aaggacgggc agattgggga gggaaaggat gttgggctaa gggctgtgag cttatgttac    3840
aggcaactga gccactgaag aattttgacg aagaaaatgc caaccaaagc agtcatttta    3900
aaagtttatg gctgttcagt tacaggacaa gttgtgaaaa gaaagaaaaa aaaaaaaaaa    3960
aaaaaa                                                              3966
```

<210> SEQ ID NO 2
<211> LENGTH: 1468
<212> TYPE: DNA
<213> ORGANISM: human

<400> SEQUENCE: 2

```
cccgggtttg gccgccccag ccccgccttc cccgcccgg ggagcccgcc ccctgccccg      60
cgtccctgcc gacagagtta gcacgacatc agtatgagct ggtcaccttc cctgacaacg     120
cagacatgtg gggcctggga aatgaaagag cgccttggga cagggggatt tggaaatgtc     180
atccgatggc acaatcaggc tgacccaccc caatgtggtg gctgcccgag atgtccctga     240
ggggatgcag aacttggcgc ccaatgacct gcccctgctg ccatggagt actgccaagg     300 aggagatctc cggaagtacc tgaaccagtt tgagaactgc tgtggtctgc gggaaggtgc     360
catcctcacc ttgctgagtg acattgcctc tgcgcttaga taccttcatg aaaacagaat     420
catccatcgg gatctaaagc cagaaaacat cgtcctgcag caaggagaac agaggttaat     480
acacaaaatt attgacctag gatatgccaa ggagctggat cagggcagtc tttgcacatc     540
attcgtgggg accctgcagt acctggcccc agagctactg gagcagcaga agtacacagt     600
gaccgtcgac tactggagct tcggcaccct ggcctttgag tgcatcacgg gcttccggcc     660
cttcctcccc aactggcagc ccgtgcagtg gcattcaaaa gtgcggcaga agagtgaggt     720
ggacattgtt gttagcgaag acttgaatgg aacggtgaag ttttcaagct ctttaccta     780 ccccaataat cttaacagtg tcctggctga gcgactggag aagtggctgc aactgatgct     840
gatgtggcac cccgacaga ggggcacgga tcccacgtat gggcccaatg gctgcttcaa      900
ggccctggat gacatcttaa acttaaagct ggttcatatc ttgaacatgg tcacgggcac     960
catccacacc taccctgtga cagaggatga gagtctgcag agcttgaagg ccagaatcca    1020
acaggacacg ggcatcccag aggaggacca ggagctgctg caggaagcgg gcctggcgtt    1080
gatccccgat aagcctgcca ctcagtgtat ttcagacggc aaggtgagcc ctggcttcgt    1140
acacaccatc ctgtttacct tggctgtgcc tcctgggaaa ctcaacacac tttcagattt    1200
caattctgct ttgtcatgta gtctgttaat cacacagtgc ggatacctgg ctggtttta    1260
```

-continued

```
agttggagta tggtgttctc tgtgtggcct gataggaaac acaaatctcc ttgctggact    1320
tgttacttcc aaaccctcca agaccggtct cttgccttta ttgcaaaaaa tgatgctata    1380
acactcgaat ctctcaagtt gcctgcttgg ccctcttcca agtgtactaa aaaaaaaaaa    1440
aaaaaaagat ctttaattaa gcggccgc                                       1468
```

<210> SEQ ID NO 3
<211> LENGTH: 1055
<212> TYPE: DNA
<213> ORGANISM: human

<400> SEQUENCE: 3

```
atgacatgat tacgaattta atacgactca ctatagggaa tttggccctc gaggccaaga      60
attcggcacg aggtgtagct gggggtaagt aacttgccaa ggggtcacac agctagaaag    120
cggtggaccc tagatgcagg cgcagccatt cagaccccac agtccacatt cctttgagcc    180
agtccattga gggtcctcag ggaatgtggc gggtcccctg gtctcgctcc cccgcagatc    240
ttgcatctca gcatgcgcct accacatcag ttgacattag cacagctttt ccattaggag    300
aacgaagtga aactcctggt agaacggatg atggctctgc agaccgacat tgtggactta    360
cagaggagcc ccatgggccg gaagcagggg ggaacgctgg acgacctaga ggagcaagca    420
agggagctgt acaggagact aagggaaaaa cctcgagacc agcgaactga gggtgacagt    480
caggaaatgg tacgggtgct gcttcaggca attcagagct tcgagaagaa agtgcgagtg    540
atctatacgc agctcagtaa aactgtggtt tgcaagcaga aggcgctgga actgttgccc    600
aaggtggaag aggtggtgag cttaatgaat gaggatgaga agactgttgt ccggctgcag    660
gagaagcggc agaaggagct ctggaatctc ctgaagattg cttgtagcaa ggtccgtggt    720
cctgtcagtg gaagcccgga tagcatgaat gcctctcgac ttagccagcc tgggcagctg    780
atgtctcagc cctccacggc ctccaacagc ttacctgagc cagccaagaa gagtgaagaa    840
ctggtggctg aagcacataa cctctgcacc ctgctagaaa atgccataca ggacactgtg    900
agggaacaag accagagttt cacggtaaca gcttgtgtga gactcctgcg attccatgtc    960
ctttctttct atggcaaaat agaagagaaa atggaaatgc aatctggcat tatcctcaac   1020
ctcaaaaaaa aaaaaaaaa aacgaaggcg gccgc                                1055
```

HUMAN IKK-BETA DNA CONSTRUCTS AND CELLS

This application claims the benefit of provisional application Ser. No. 60/068,954 filed Dec. 30, 1997, which is incorporated herein by reference.

TECHNICAL FIELD OF THE INVENTION

This invention is related to a novel kinase involved in regulation of the NFκB transcription factors.

BACKGROUND OF THE INVENTION

IκB comprises, a family of regulatory molecules for the NFκB transcription factor family. The NIEκB factors are important effectors of function of a number of pro-inflammatory factors, such as cytokines (e.g., IL-1, IL-6, IL-8, and TNF) and the redox system (reduction/oxidation). The regulation of the activation of NFκB is an important target for therapeutic intervention of inflammatory diseases.

The activation of NFκB by diverse pro-inflammatory factors involves a cascade of molecules from the cell surface receptors of the cytokines to the cytosolic signaling molecules. The final and common step of NFκB activation is controlled by the IκB family of molecules. The IκB family consists of IκBα, IκBβ, IκBγ, and other IκB related proteins, such as Bcl-3, which inhibit the nuclear translocation and DNA binding of NFκB through complex formation with the NFκB family of factors in both the cytoplasm and the nucleus. The final activation of NFκB is achieved through the phosphorylation and subsequent degradation of the complexed IκB protein, which releases the NFκB factor to be translocated into the nucleus and bound to NFκB-specific DNA sequences in the promoters of NFκB target genes, functioning as a transcriptional activator.

The diverse initial activation factors of NFκB converge into the final step of activation of IκB kinase (IKK), which specifically phosphorylates the inhibitory IκB factor and results in subsequent degradation of IκB factors. IKK proteins are therefore critical targets for anti-inflammatory drug development. Thus, there is a need in the art for identifying new components of this important regulatory system.

SUMMARY OF THE INVENTION

It is an object of the present invention to provide therapeutic tools to treat inflammation. This and other objects of the invention are provided by one or more of the embodiments described below.

One embodiment of the invention is an isolated and purified human IKKβ protein which is at least 85% identical to a protein encoded by a polynucleotide comprising a nucleotide sequence selected from the group consisting of SEQ ID NOS:1, 2, and 3. Percent identity is determined using a Smith-Waterman homology search algorithm using an affine gap search with a gap open penalty of 12 and a gap extension penalty of 1.

Another embodiment of the invention is an isolated and purified polypeptide comprising at least 8 contiguous amino acids of an amino acid sequence encoded by a nucleotide sequence selected from the group consisting of SEQ ID NOS:1, 2, and 3.

Even another embodiment of the invention is a fusion protein comprising a first protein segment and a second protein segment fused to each other by means of a peptide bond. The first protein segment consists of at least 8 contiguous amino acids of an amino acid sequence encoded by a polynucleotide comprising a nucleotide sequence selected from the group consisting of SEQ ID NOS:1, 2, and 3.

Still another embodiment of the invention is a preparation of antibodies which specifically bind to a protein having an amino acid sequence encoded by a polynucleotide comprising a nucleotide sequence selected from the group consisting of SEQ ID NOS:1, 2, and 3.

A further embodiment of the invention is a cDNA molecule which encodes a protein having an amino acid sequence which is at least 85% identical to an amino acid sequence encoded by a polynucleotide comprising a nucleotide sequence selected from the group consisting of SEQ ID NOS:1, 2, and 3. Percent identity is determined using a Smith-Waterman homology search algorithm using an affine gap search with a gap open penalty of 12 and a gap extension penalty of 1.

Yet another embodiment of the invention is a cDNA molecule which is at least 85% identical to a nucleotide sequence selected from the group consisting of SEQ ID NOS:1, 2, and 3. Percent identity is determined using a Smith-Waterman homology search algorithm using, an affine gap search with a gap open penalty of 12 and a gap extension penalty of 1.

Another embodiment of the invention is an isolated and purified subgenomic polynucleotide comprising a nucleotide sequence which hybridizes to a nucleotide sequence selected from the group consisting of SEQ ID NOS:1, 2, and 3 after washing with 0.2 xSSC at 65° C.

Even another embodiment of the invention is a construct comprising a promoter and a polynucleotide segment comprising at least 12 contiguous nucleotides of a nucleotide sequence selected from the group consisting of SEQ ID NOS:1, 2, and 3. The polynucleotide segment is located downstream from the promoter. Transcription of the polynucleotide segment initiates at the promoter.

Still another embodiment of the invention is a host cell comprising a construct which comprises a promoter and a polynucleotide segment comprising at least 12 contiguous nucleotides of a nucleotide sequence selected from the group consisting of SEQ ID NOS:1, 2, and 3.

A further embodiment of the invention is a homologously recombinant cell having incorporated therein a new transcription initiation unit. The new transcription initiation unit comprises (a) an exogenous regulatory sequence, (b) an exogenous exon, and (c) a splice donor site. The new transcription initiation unit is located upstream of a coding sequence of a gene. The gene has a coding sequence selected from the group consisting of SEQ ID NOS:1, 2, and 3. The exogenous regulatory sequence directs transcription of the coding sequence of the gene.

Yet another embodiment of the invention is a method of screening test compounds for use as inflammation inhibitors. A test compound is contacted with an IKKβ protein encoded by a polynucleotide comprising a nucleotide sequence selected from the group consisting of SEQ ID NOS:1, 2, and 3. The contacted IKKβ protein for its ability to bind to or phosphorylate IκB. A test compound which inhibits phosphorylation of IκB by the IKKβ protein or which inhibits the binding of the IKKβ protein to IκB is a candidate drug for treatment of inflammation.

These and other embodiments of the invention provide the art with a new therapeutic target for immediate use as well as for development of other therapeutic agents which interact with IKKβ.

DETAILED DESCRIPTION OF THE INVENTION

A gene which encodes novel forms of IκB kinase (IKKβ), i.e., an enzyme which phosphorylates IκB, is a discovery of the present invention. The full-length coding sequence of IKKβ is shown in SEQ ID NO:1. SEQ ID NO:2 is the nucleotide sequence which encodes the N-terminal kinase domain of IKKβ. SEQ ID NO:3 is the nucleotide sequence which encodes the C-terminal HLH domain of IKKβ. The proteins encoded by SEQ ID NOS:2 and 3 may be alternatively spliced forms of IKKβ. These forms may function to regulate the function of IKKβ as a dominant positive or dominant negative IKKβ. Thus, the two forms of IKKβ may be used as therapeutic agents to regulate the NFκB pathway, which is involved in inflammatory diseases and cancer.

IKKβ proteins of the invention include naturally and non-naturally occurring variants. For example, any naturally occurring variants of forms of IKKβ which may occur in human tissues and which bind to and phosphorylate IκB are biologically active IKKβ variants and are within the scope of this invention. Non-naturally occurring IKKβ variants which contain conservative amino acid substitutions relative to the amino acid sequences encoded by SEQ ID NOS:1, 2, or 3 but which retain substantially the same kinase activity as naturally occurring IKKβ variants are also biologically active human IKKβ variants of the invention. Guidance in determining which amino acid residues may be substituted, inserted, or deleted without abolishing biological or immunological activity of IKKβ may be found using computer programs well known in the art, such as DNASTAR software.

Preferably, amino acid substitutions in biologically active IKKβ variants are conservative amino acid changes, i.e., substitutions of similarly charged or uncharged amino acids. A conservative amino acid change involves substitution of one of a family of amino acids; which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, in aspartate with a glutamate, a threonine with a serine, or a similar replacement of an amino acid with a structurally related amino acid will not have a major effect on the binding properties of the resulting molecule, especially if the replacement does not involve an amino acid at the IκB-binding site of IKKβ or its kinase domain. Whether an amino acid change results in a functional IKKβ protein or polypeptide can readily be determined by assaying its ability to phosphorylate or bind to IκB. In vitro kinase assays are taught, for example, in WO 96/36642. Binding to IκB can be determined, inter alia, using a yeast two-hybrid assay (Fields & Song, *Nature* 340, 245–46, 1989). Alternatively, complex formation can be detected by observing altered mobility on non-denaturing gels or by co-immunoprecipitation.

Biologically active IKKβ variants include glycosylated forms, aggregative conjugates with other molecules, and covalent conjugates with unrelated chemical moieties. Covalent variants can be prepared by linking functionalities to groups which are found in the amino acid chain or at the N- or C-terminal residue, as is known in the art. Biologically active IKKβ variants also include allelic variants, species variants, and muteins,. Truncations or deletions of regions which do not affect the kinase activity of IKKβ are also IKKβ variants.

Preferred naturally or non-naturally occurring biologically active IKKβ variants have amino acid sequences which are at least 85%, 90%, 95%, 96%, or 97% identical to amino acid sequences encoded by a polynucleotide having a coding sequence as shown in SEQ ID NOS:1, 2, and 3. More preferably, the molecules are at least 98% or 99% identical. Percent identity is determined according to the Smith-Waterman homology search algorithm, using an affine gap search with the following parameters: a gap opener penalty of 12 and a gap extension penalty of 1. The Smith-Waterman homology search algorithm is taught in Smith and Waterman, *Adv. Appl. Math.* (1981) 2: 482–489.

IKKβ polypeptides contain less than full-length IKKβ and comprise at least 6, 8, 10, 12, 15, 20, 50, 100, 200, 250, 300, 350, 400, 450, 500, 550, 600, 650, 700, 750, 800, 850, 900, 950, 1000, 1050, 1100, 1150, 1200, 1250, or 1300 or more contiguous amino acids of a full-length IKKβ protein encoded by SEQ ID NO:1. IKKβ polypeptides can also comprise at least 6, 8, 10, 12, 15, 20, 50, 100, 200, 250, 300, 350, or 400 or more contiguous amino acids of the N-terminal kinase domain of IKKβ encoded by SEQ ID NO:2, or at least 6, 8, 10, 12, 15, 20, 50, 100, 200, 250, or 300 or more contiguous amino acids of the C-terminal protein interacting domain of IKKβ encoded by SEQ ID NO:3. Alternatively, IKKβ polypeptides can encode the entire N-terminal kinzisc domain or C-terminal protein interacting domain of IKKβ.

IKKβ can be isolated from IKKβ-producing human cells, such as heart, brain, lung, liver, muscle, kidney, and testis. IKKβ can be obtained substantially free from other human proteins by standard protein purification methods, such as size exclusion chromatography, ion exchange chromatography, ammonium sulfate fractionation, affinity chromatography, or preparative gel electrophoresis.

Alternatively, synthetic chemical methods, such as solid phase peptide synthesis, can be used to synthesize an IKKβ protein or polypeptide. General means for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, B. Weinstein, ed. (1983). Moreover, substitution of D-amino acids for the normal L-stereoisomer can be carried out to increase the half-life of the molecule. Biologically active IKKβ or altered variants can be similarly produced.

IKKβ protein or polypeptides can also be produced recombinantly, by expressing IKKβ coding sequences selected from SEQ ID NOS:1, 2, or 3 in prokaryotic or eukaryotic host cells, such as bacteria, yeast, insect, or mammalian cells, using expression vectors known in the art (see below). Enzymes can be used to generate IKKβ polypeptides by enzymatic proteolysis of full-length IKKβ protein.

IKKβ protein or polypeptides can also be used in a fusion protein, for example as an immunogen. For example, IKKβ fusion proteins can be used to identify proteins which interact with IKKβ protein, such as different cyclins, and influence its function. Physical methods, such as protein affinity chromatography, or library-based assays for protein-protein interactions, such as the yeast two-hybrid or phage display systems, can also be used for this purpose. Such methods are well known in the art and can also be used as drug screens.

The fusion protein comprises two protein segments. The first protein segment can consist of at least 6, 8, 10, 12, 15, 20, 50, 100, 200, 250, 300, 350, 400, 450, 500, 550, 600, 650, 700, 750, 800, 850, 900, 950, 1000, 1050, 1100, 1150, 1200, 1250, or 1300 or more contiguous amino acids of a full-length IKKβ protein encoded by SEQ ID NO:1, at least 6, 8, 10, 12, 15, 20, 50, 100, 200, 250, 300, 350, or 400 or more contiguous amino acids of the N-terminal kinase domain of IKKβ encoded by SEQ ID NO:2, or at least 6, 8, 10, 12, 15, 20, 50, 100, 200, 250, or 300 or more contiguous amino acids of the C-terminal protein interacting domain of IKKβ encoded by SEQ ID NO:3. The first protein segment can also consist of full-length IKKβ, the entire N-terminal kinase domain of IKKβ, or the entire C-terminal protein interacting domain of IKKβ. The first protein segment is fused to a second protein segment by means of a peptide bond. The first protein segment can be N-terminal or C-terminal, as is convenient.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transfuse (GST), luciferase, horseradish peroxidase (HRP), and chloramphenicol acetyltransferase (CAT). Epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fusions, and herpes simplex virus (HSV) BP16 protein fusions.

IKKβ fusion proteins can be made by covalently linking the first and second protein segments or by standard procedures in the art of molecular biology. Recombinant DNA methods can be used to prepare IKKβ fusion proteins, for example, by making a DNA construct which comprises coding sequences selected from SEQ ID NOS:1, 2, or 3 in proper reading frame with nucleotides encoding the second protein segment and expressing the DNA construct in a host cell, as is known in the art. Many kits for constructing fusion proteins are available from companies which supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Isolated and purified IKKβ proteins, polypeptides, biologically active or altered variants, or fusion proteins can be used as immunogens, to obtain preparations of antibodies which specifically bind to epitopes of an IKKβ protein encoded by a polynucleotide comprising a nucleotide sequence of SEQ ID NOS:1, 2, or 3 or a biologically active or altered IKKβ variant. Preferably, the antibodies can distinguish between IKKβ and other cyclin-dependent kinases, for example by binding to the cyclin-binding site of IKKβ. Typically, at least 6, 8, 10, or 12 contiguous amino acids are required to form an IKKβ epitope. However, epitopes which involve non-contiguous amino acids may require more, e.g., at least 15, 25, or 50 amino acids.

Antibodies which specifically bind to epitopes of IKKβ proteins, polypeptides, fusion proteins, or biologically active variants can be used in immunochemical assays, including but not limited to Western blots, ELISAs, radioimmunoassays, immunohistochemical assays, immunoprecipitations, or other immunochemical assays known in the art. Typically, antibodies of the invention provide a detection signal at least 5-, 10-, or 20-fold higher than a detection signal provided with other proteins when used in such immunochemical assays. Preferably, antibodies which specifically bind to IKKβ epitopes do not detect other proteins in immunochemical assays and can immunoprecipitate IKKβ protein or polypeptides from solution.

Epitopes of IKKβ which are particularly antigenic can be selected, for example, by routine screening of IKKβ polypeptides for antigenicity or by applying a theoretical method for selecting antigenic regions of a protein to the amino acid sequences encoded by SEQ ID NOS:1, 2, or 3. Such methods are taught, for example, in Hopp and Wood, *Proc. Natl. Acad. Sci. U.S.A.* 78, 3824–28 (1981), Hopp and Wood, *Mol. Immunol.* 20, 483–89 (1983), and Sutcliffe et al., *Science* 219, 660–66 (1983).

Any type of antibody known in the art can be generated to bind specifically to IKKβ epitopes. For example, preparations of polyclonal and monoclonal antibodies can be made using standard methods which are well known in the art. Similarly, single-chain antibodies can also be prepared. Single-chain antibodies which specifically bind to IKKβ epitopes can be isolated, for example, from single-chain immunoglobulin display libraries, as is known in the art. The library is "panned" against IKKβ amino acid sequences, and a number of single chain antibodies which bind with high-affinity to different epitopes of IKKβ protein can be isolated. Hayashi et al., 1995, *Gene* 160: 129–30. Single-chain antibodies can also be constructed using a DNA amplification method, such as the polymerase chain reaction (PCR), using hybridoma cDNA as a template. Thirion et al., 1996, *Eur. J Cancer Prev.* 5: 507–11.

Single-chain antibodies can be mono- or bispecific, and can be bivalent or tetravalent. Construction of tetravalent, bispecific single-chain antibodies is taught, for example, in Coloma and Morrison, 1997, *Nat. Biotechnol.* 15: 159–63. Construction of bivalent, bispecific single-chain antibodies is taught inter alia in Mallender and Voss, 1994, *J. Biol. Chem.* 269: 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61: 497–501; Nicholls et al., 1993, *J. Immunol. Meth.* 165: 81–91.

Monoclonal and other antibodies can also be "humanized" in order to prevent a patient from mounting an immune response against the antibody when it is used therapeutically. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grafting of entire complementary determining regions. Alternatively, one can produce humanized antibodies using recombinant methods, as described in GB2188638B. Antibodies which specifically bind to IKKβ epitopes can contain antigen binding sites which are either partially or fully humanized, as disclosed in U.S. Pat. No. 5,565,332.

Other types of antibodies can be constructed and used in methods of the invention. For example, chimeric antibodies can be constructed as disclosed, for example, in WO 913/03151. Binding proteins which are derived from immunoglobulins and which are multivalent and multispecific, such as the "diabodies" described in WO 94/1.3804, can also be prepared.

Antibodies of the invention can be purified by methods well known in the art. For example, antibodies can be affinity purified by passing the antibodies over a column to which an IKKβ protein, polypeptide, biologically active variant, or fusion protein is bound. The bound antibodies can then be eluted from the column, using a buffer with a high salt concentration.

IKKβ-specific binding polypeptides other than antibodies can also be generated. IKKβ-specific binding polypeptides are polypeptides which bind with IKKβ or its variants and which have a measurably higher binding affinity for IKKβ and polypeptide derivatives of IKKβ than for other polypeptides tested for binding. Higher affinity by a factor of 10 is preferred, more preferably a factor of 100. Such polypeptides can be found, for example, using the yeast two-hybrid system.

Antibodies can be used, inter alia, to detect wild-type IKKβ protein in human tissue and fractions thereof. The antibodies can also be used to detect the presence of mutations in the IKKβ gene which result in under- or overexpression of an IKKβ protein or in expression of an IKKβ protein with altered size or electrophoretic mobility. Optionally, antibodies of the invention can be used to alter effective levels of functional IKKβ protein.

The invention also provides subgenomic polynucleotides which encode IKKβ proteins, polypeptides, biologically active or altered variants, fusion proteins, and the like. IKKβ subgenomic polynucleotides contain less than a whole chromosome and can be double- or single-stranded. Preferably, the polynucleotides are intron-free.

IKKβ subgenomic polynucleotides can comprise at least 11, 12, 15, 18, 24, 50, 75, 100, 200, 300, 400, 500, 750, 1000, 1250, 1500, 1750, 2000, 2250, 2500, 2750, 3000, 3250, 3500, or 3750 or more contiguous nucleotides of SEQ ID NO:1, at least 11, 12, 15, 18, 24, 50, 75, 100, 200, 300, 400, 500, 750, 1000, 1250, 1300, 1350, or 1400 or more contiguous nucleotides of SEQ ID NO:2, or at least 11, 12, 15, 18, 24, 50, 75, 100, 200, 300, 400, 500, 750, or 1000 contiguous nucleotides of SEQ ID NO:3 or their complements. Complementary nucleotide sequences can be used provide IKKβ antisense oligonucleotides. IKKβ subgenomic polynucleotides also include polynucleotides which encode IKKβ-specific single-chain antibodies, ribozymes, and biologically active or altered IKKβ variants.

Degenerate nucleotide sequences encoding amino acid sequences of IKKβ protein or biologically active IKKβ variants, as well as homologous nucleotide sequences which are at least 65%, 75%, 85%, 90%, 95%, 96%, 97%, 98%, or 99% identical to the nucleotide sequences shown in SEQ ID NOS:1, 2, or 3 are also IKKβ subgenomic polynucleotides. Percent sequence identity is determined using computer programs which employ the Smith-Waterman algorithm, for example as implemented in the MPSRCH program (Oxford Molecular), using an affine gap search with the following parameters: a gap open penalty of 12 and a gap extension penalty of 1.

Nucleotide sequences which hybridize to the coding sequences shown in SEQ ID NOS:1, 2, and 3 or their complements with at most 1, 2, 3, 4, 5, 10, 15, 20, 25, 30, or 35% basepair mismatches are also IKKβ subgenomic polynucleotides of the invention. For example, using the following wash conditions—2 ×SSC (0.3 M sodium chloride, 0.03 M sodium citrate, pH 7.0), 0.1% SDS, room temperature twice, 30 minutes each; then 2 ×SSC, 0.1% SDS, 50° C. once, 30 minutes; then 2 ×SSC, room temperature twice, 10 minutes each—homologous IKKβ sequences can be identified which contain at most about 25–30% basepair mismatches with SEQ ID NOS: 1, 2, or 3 or their complements. More preferably, homologous nucleic acid strands contain 15–25% basepair mismatches, even more preferably 5–15% basepair mismatches.

Species homologs of IKKβ subgenomic polynucleotides of the invention can also be identified by making suitable probes or primers and screening cDNA expression libraries from other species, such as mice, monkeys, yeast, or bacteria. It is well known that the $T_m$ of a double-stranded DNA decreases by 1–1.5° C. with every 1% decrease in homology (Bonner et al., *J.MoL Biol.* 81, 123 (1973). Homologous IKKβ polynucleotides can therefore be identified, for example, by hybridizing a putative homologous IKKβ polynucleotide with a polynucleotide having the nucleotide sequence of SEQ ID NOS:1, 2, or 3, comparing the melting temperature of the test hybrid with the melting temperature of a hybrid comprising a polynucleotide having SEQ ID NOS:1, 2, or 3 and a polynucleotide which is perfectly complementary to that sequence, and calculating the number or percent of basepair mismatches within the test hybrid.

Nucleotide sequences which hybridize to the coding sequences shown in SEQ ID NOS:1, 2, or 3 or their complements following stringent hybridization and/or wash conditions are also IKKβ subgenomic polynucleotides of the invention. Stringent wash conditions are well known and understood in the art and are disclosed, for example, in Sambrook; et al., MOLECULAR CLONING: A LABORATORY MANUAL, 2d ed., 1989, at pages 9.50–9.51.

Typically, for stringent hybridization conditions, a combination of temperature and salt concentration should be chosen that is approximately 12–20° C. below the calculated $T_m$ of the hybrid under study. The $T_m$ of a hybrid between the IKKβ sequence shown in SEQ ID NOS:1, 2, or 3 and a polynucleotide sequence which is 65%, 75%, 85%, 90%, 95%, 96%, 97%, 98%, or 99% identical can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\%G+C) - 0.63(\%\text{formamide}) - 600/l,$$

where l=the length of the hybrid in basepairs.

Stringent wash conditions include, for example, 4 ×SSC at 65° C., or 50% formamide, 4 ×SSC at 42° C., or 0.5 ×SSC, 0.1% SDS at 65° C. Highly stringent wash conditions include, for example, 0.2 ×SSC at 65° C.

IKKβ subgenomic polynucleotides can be isolated and purified free from other nucleotide sequences using standard nucleic acid purification techniques. For example, restriction enzymes and probes can be used to isolate polynucleotide fragments which comprise nucleotide sequences encoding an IKKβ protein or variant. Isolated and purified subgenomic polynucleotides are in preparations which are free or at least 90% free of other molecules.

Complementary DNA (cDNA) molecules which encode IKKβ proteins are also IKKβ subgenomic polynucleotides of the invention. IKKβ cDNA molecules can be made with standard molecular biology techniques, using IKKβ mRNA as a template. IKKβ cDNA molecules can thereafter be replicated using molecular biology techniques known in the art and disclosed in manuals such as Sambrook et al., 1989. An amplification technique, such as the polymerase chain reaction (PCR), can be used to obtain additional copies of subgenomic polynucleotides of the invention, using either human genomic DNA or cDNA as a template.

Alternatively, synthetic chemistry techniques can be used to synthesize IKKβ subgenomic polynucleotide molecules of the invention. The degeneracy of the genetic code allows alternate nucleotide sequences to be synthesized which will encode IKKβ proteins or biologically active variants. All such nucleotide sequences are within the scope of the present invention.

The invention also provides polynucleotide probes which can be used to detect IKKβ sequences, for example, in hybridization protocols such as Northern or Southern blotting or in situ hybridization. Polynucleotide probes of the invention comprise at least 12, 13, 14, 15, 16, 17, 18, 19, 20, 30, or 40 or more contiguous nucleotides selected from SEQ ID NOS:1, 2, or 3. Polynucleotide probes of the invention can comprise a detectable label, such as a radioisotopic, fluorescent, enzymatic, or chemiluminescent label.

An IKKβ construct can be an expression construct which comprises a promoter which is functional in a selected host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes, for example, all or a portion of an IKKβ protein, variant, fusion protein, antibody, or ribozyme. The polynucleotide segment is located downstream from the promoter. Transcription of the polynucleotide segment initiates at the promoter.

A recombinant host cell comprising an IKKβ construct can be constructed, for example, to express all or a portion of an IKKβ protein. Recombinant host cells comprising IKKβ expression constructs can be prokaryotic or eukaryotic. A variety of host cells are available for use in bacterial, yeast, insect, and human expression systems and can be used to express or to propagate IKKβ expression constructs.

Constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

Bacterial systems for expressing IKKβ expression constructs include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Nat. Acad Sci. USA* (1983) 80: 21–25, and Siebenlist et al., *Cell* (1980) 20: 269.

Expression systems in yeast include those described in Hinnen et al., *Proc. Nati Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al.,*J. Gen. Microbiol.* (1986) 132: 3459, Roggenkamp et al., *Mol Gen. Genet.* (1986) 202 :302) Das et al., *J. Bacteriol.* (1984)158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al.,*Mol. Cell. Biol.* (1985) 5: 3376, U.S. Pat. No. 4,837,148, U.S. Pat. No. 4,929,555; Beach and Nurse,*Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et al., *Gene* (1983) 26: 205–221, Yelton et al., *Proc. Natl. Acad. Sci. USA* (1984) 81: 1470–1474, Kelly and Hynes, *EMBO J.* (1985) 4: 475479; EP 244,234, and WO 91/00357.

Expression of IKKβ expression constructs in insects can be carried out as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al.,*J. Gen. Virol.* (1988) 69: 765–776, Miller et al.,*Ann. Rev. Microbiol.* (1988) 42: 177, Carbonell et al., *Gene* (1988) 73: 409, Maeda et al., *Nature* (1985) 315: 592–594, Lebacq-Verheyden et al.,*Mol. Cell. Biol.* (1988) 8: 3129: Smith et al., *Proc. Natl. Acad. Sci. USA* (1985) 82: 8404, Miyajima et al., *Gene* (1987)58: 273; and Martin et al., *DNA* (1988) 7:99. Numerous baculoviral strains and variants and corresponding permissive insect host cells from hosts are described in Luckow et al., *Bio/Technology* (1988) 6: 47–55, Miller et al., in GENETIC ENGINEERING (Setlow, J. K. et al. eds.), Vol. 8 (Plenum Publishing, 1986), pp. 277–279, and Maeda et al., *Nature,* (1985) 315: 592–594.

Mammalian expression of IKKβ expression constructs can be achieved as described in Dijkema et al., *EMBO J.* (1985) 4: 761, Gorman et al., *Proc. Natl. Acad. Sci. USA* (1982b) 79: 6777, Boshart et al., *Cell* (1985) 41: 521 and U.S. Pat. No. 4,399,216. Other features of mammalian expression of IKKβ expression constructs can be facilitated as described in Ham and Wallace, Meth. Enz. (1979) 58: 44, Barnes and Sato,*Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. RE 30,985.

Subgenomic polynucleotides of the invention can also be used in gene delivery vehicles, for the purpose of delivering an IKKβ mRNA or oligonucleotide (either with the sequence of native IKKβ mRNA or its complement), full-length IKKβ protein, IKKβ fusion protein, IKKβ polypeptide, biologically active or altered variant, or IKKβ-specific ribozyme or single-chain antibody into a cell, preferably a eukaryotic cell. According to the present invention, a gene delivery vehicle can be, for example, naked plasmid DNA, a viral expression vector comprising an IKKβ subgenomic polynucleotide, or an IKKβ subgenomic polynucleotide in conjunction with a liposome or a condensing agent.

In one embodiment of the invention, the gene delivery vehicle comprises a promoter and an IKKβ subgenomic polynucleotide. Preferred promoters are tissue-specific promoters and promoters which are activated by cellular proliferation, such as the thymidine kinase and thymidylate synthase promoters. Other preferred promoters include promoters which are activatable by infection with a virus, such as the α-and β-interferon promoters, and promoters which are activatable by a hormone, such as estrogen. Other promoters which can be used include the Moloney virus LTR, the CMV promoter, and the mouse albumin promoter.

An IKKβ gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornaviris, poxvirus, retrovirus, togavirus or adenovirus. In a preferred embodiment, the IKKβ gene delivery vehicle is a recombinant retroviral vector. Recombinant retroviruses and various uses thereof have been described in numerous references including, for example, Mann et al., *Cell* 33: 153, 1983, Cane and Mulligan, *Proc. Natl. Acad. Sci. USA* 81: 6349, 1984, Miller et al.,*Human Gene Therapy* 1:5–14, 1990, U.S. Pat. Nos. 4,405,712,4,861,719, and 4,980,289, and PCT Application Nos. WO 89/02,468, WO 89/05,349, and WO 90/02,806.

Numerous retroviral gene delivery vehicles can be utilized in the present invention, including for example those described in EP 0,415,731; WO 90/07936; WO 94/03622; WO 93/256598; WO 93/25234; U.S. Pat. No. 5,219,740; WO 9311230; WO 9310218; Vile and Hart, *Cancer Res.* 53: 3860–3864, 1993; Vile and Hart, *Cancer Res.* 53: 962–967, 1993; Ram et al, *Cancer Res.* 53: 83–88, 1993; Takamiya et al., *J. Neurosci. Res.* 33: 493–503, 1992; Baba et al., *J. Neurosurg.* 79: 729–735, 1993 (U.S. Pat. No. 4,777,127, GB 2,200,651, EP 0,345,242 and WO91/02805).

Particularly preferred retroviruses are derived from retroviruses which include avian leukosis virus (ATCC Nos. VR-535 and VR-247), bovine leukemia virus (VR-1315), murine leukemia virus (MLV), mink-cell focus-inducing virus (Koch et al., *J. Vir.* 49: 828,1984; and Oliffet al., *J. Vir.* 48: 542,1983), murine sarcoma virus (ATCC Nos. VR-844, 45010 and 45016), reticuloendotheliosis virus (ATCC Nos VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector.

Particularly preferred strains of MLV from which recombinant retroviruses can be generated include 4070A and 1504A (Hartley and Rowe, *J. Vir.* 19: 19, 1976), Abelson (ATCC No. VR-999), Friend (ATCC No. VR-245), Graffi (Ru et al., *J. Vir.* 67: 4722, 1993; and Yantchev *Neoplasma* 26: 397, 1979), Gross (ATCC No. VR-590), Kirsten (Albino et al., *J. Exp. Med.* 164: 1710, 1986), Harvey sarcoma virus (Manly et al., *J. Vir.* 62: 3540, 1988; and Albino et al., *J. Exp. Med.* 164: 1710, 1986) and Rauscher (ATCC No. VR-998), and Moloney MLV (ATCC No. VR-190).

A particularly preferred non-mouse retrovirus is Rous sarcoma virus. Preferred Rous sarcoma viruses include Bratislava (Manly et al., *J. Vir.* 62: 3540, 1988; and Albino et al., *J. Exp. Med.* 164: 1710, 1986), Bryan high titer (e.g., ATCC Nos. VR-334, VR-657, VR-726, VR-659, and VR-728), Bryan standard (ATCC No. VR- 140), Carr-Zilber (Adgighitov et al., *Neoplasma* 27: 159, 1980), Engelbreth-Holm (Laurent et al., *Biochem Biophys Acta* 908: 241, 1987), Harris, Prague (e.g., ATCC Nos. VR-772, and 45033), and Schmidt-Ruppin (e.g. ATCC Nos. VR-724, VR-725, VR-354) viruses.

Any of the above retroviruses can be readily utilized in order to assemble or construct retroviral IKKβ gene delivery vehicles given the disclosure provided herein and standard recombinant techniques (e.g., Sambrook et al., *Molecular Cloning: A Laboratory Manual,* 2d ed., Cold Spring Harbor Laboratory Press, 1989, and Kunkle, *PROC. NATL. ACAD. SCI. U.S.A.* 82: 488, 1985) known in the art. Portions of retroviral IKKβ expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus.

Recombinant retroviral vectors can be used to generate transduction competent retroviral vector particles by introducing them into appropriate packaging cell lines (see Ser. No. 07/800,921, filed Nov. 29, 1991). Recombinant retroviruses can be produced which direct the site-specific integration of the recombinant retroviral genome into specific regions of the host cell DNA. Site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus.

Packaging cell lines suitable for use with the above-described retroviral gene delivery vehicles can be readily prepared (see Ser. No. 08/240,030, filed May 9, 1994; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805.

Recombinant retroviral gene delivery vehicles can be used to generate transduction competent retroviral particles by introducing them into appropriate packaging cell lines (see Ser. No. 07/800,921). Similarly, adenovirus gene delivery vehicles can also be readily prepared and utilized given the disclosure provided herein (see also Berkner, *Biotechniques* 6: 616–627, 1988, and Rosenfeld et al., *Science* 252: 431–434, 1991, WO 93/07283, WO 93/06223, and WO 93/07282).

An IKKβ gene delivery vehicle can also be a recombinant adenoviral gene delivery vehicle. Such vehicles can be readily prepared and utilized given the disclosure provided herein (see Berkner, *Biotechniques* 6: 616, 1988, and Rosenfeld et al., *Science* 252: 431, 1991, WO 93/07283, WO 93/06223, and WO 93/07282). Adeno-associated viral IKKβ gene delivery vehicles can also be constructed and used to deliver IKKβ amino acids or nucleotides.

The use of adeno-associated viral gene delivery vehicles in vitro is described in Chatterjee et al., *Science* 258: 1485–1488 (1992), Walsh et al., *Proc. Nat'l. Acad. Sci.* 89: 7257–7261 (1992), Walsh et al., *J. Clin. Invest.* 94: 1440–1448 (1994), Flotte et al., *J. Biol. Chem.* 268: 3781–3790 (1993), Ponnazhagan et al., *J. Exp. Med* 179: 733–738 (1994), Miller et al., *Proc. Nat'l Acad. Sci.* 91. 10183–10187 (1994), Einerhand et al., *Gene Ther.* 2: 336–343 (1995), Luo et al., *Exp. Hematol.* 23: 1261–1267 (1995), and Zhou et al., *Gene Therapy* 3: 223–229 (1996). In vivo use of these vehicles is described in Flotte et al., *Proc. Nat'l Acad. Sci.* 90: 10613–10617 (1993), and Kaplitt et al., *Nature Genet.* 8: 148–153 (1994).

In another embodiment of the invention, an IKKβ gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for IKKβ polynucleotides. Alpha viruses are described in WO 94/21792, WO 92/10578 and WO 95/07994. Several different alphavirus gene delivery vehicle systems can be constructed and used to deliver IKKβ subgenomic polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627.

Preferably, the recombinant viral vehicle is a recombinant alphavirus viral vehicle based on a Sindbis virus. Sindbis constructs, as well as numerous similar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis non-structural proteins, a viral junction region inactivated so as to prevent subgenomic fragment transcription, and a Sindbis RNA polymerase recognition sequence. Optionally, the viral junction region can be modified so that subgenomic polynucleotide transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region which has been inactivated in order to prevent transcription of the subgenomic polynucleotide and a second viral junction region which has been modified such that subgenomic polynucleotide transcription is reduced. An alphavirus-derived vehicle can also include a 5' promoter capable of initiating synthesis of viral RNA from CDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578. The Sindbis vehicles described above, as well as numerous similar constructs, can be readily prepared essentially as described in U.S. Ser. No. 08/198,450.

Other viral gere delivery vehicles suitable for use in the present invention include, for example, those derived from poliovirus (Evans et al., *Nature* 339: 385, 1989, and Sabin et al., *J. Biol. Standardization* 1: 115, 1973) (ATCC VR-58); rhinovirus (Arnold et al., *J. Cell. Biochem.* L401, 1990) (ATCC VR-1110); pox viruses, such as canary pox virus or vaccinia virus (Fisher-Hoch et al., *PROC. NATL. ACAD. SCI. U.S.A.* 86: 317,1989; Flexner et al., *Ann. N.Y Acad. Sci.* 569: 86, 1989; Flexner et al., *Vaccine*, 8: 17, 1990; U.S. Pat. No. 4,603,112 and U.S. Pat. No. 4,769,330; WO 89/01973) (ATCC VR-111; ATCC VR-2010); SV40 (Mulligan et al., *Nature* 277: 108, 1979) (ATCC VR-305), (Madzak et al., *J. Gen. Vir.* 73: 1533, 1992); and influenza virus (Luytjes et al., *Cell* 551: 1107, 1989; McMicheal et al., *The New England Journal of Medicine* 309: 13, 1983; and Yap et al., *Nature* 273: 238, 1978) (ATCC VR-797).

Other viruses which can be used to derive gene delivery vehicles include parvoviruses such as adeno-associated virus (Samulski et al., *J. Vir.* 63: 3822, 1989, and Mendelson et al., *Virology* 166: 154, 1988) (ATCC VR-645); herpes simplex virus (Kit et al., *Adv. Exp. Med. Biol.* 215: 219, 1989) (ATCC VR-977; ATCC VR-260); *Nature* 277: 108, 1979; human immunodeficiency virus (EPO 386,882, Buchschacher et al., *J. Vir.* 66: 2731,1992); and measles virus (EPO 440,219) (ATCC VR-24); A (ATCC VR-67; ATCC VR-1247).

Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Toriate (ATCC VR-925), Triniti (ATCC VR-469), Una (ATCC VR-374), Whataroa (ATCC VR-926), Y-62-33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre el al., *Proc. Soc. Exp. Biol. Med.* 121: 190, 1966) (ATCC VR-740) can also be used to provide gene delivery vehicles.

An IKKβ subgenomic polynucleotide of the invention can be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, Ser. No.08/366,787, filed Dec. 30, 1994).

Alternatively, an IKKβ subgenomic polynucleotide can be with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes.

Additionally, because a liposome is a synthetic structure, specially designed liposomes can be produced which incorporate desirable features. See Stryer, *Biochemistry*, pp. 236–240, 1975 (W. H. Freeman, San Francisco, Calif.); Szoka et al., *Biochim. Biophys. Acta* 600:1, 1980; Bayer et al., *Biochim. Biophys. Acta.* 550: 464, 1979; Rivnay et al., *Meth. Enzymol.* 149: 119, 1987; Wang et al., *PROC. NATL. ACAD. SCI. U.S.A.* 84: 7851, 1987, Plant et al., *Anal. Biochem.* 176: 420, 1989, and U.S. Pat. Nos. 4,762,915. Liposomes can encapsulate a variety of nucleic acid molecules including DNA, RNA, plasmids, and expression constructs comprising IKKβ subgenomic polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., *Proc. Natl. Acad. Sci. USA* 84: 7413–7416, 1987), mRNA (Malone et al., *Proc. Natl. Acad. Sci. USA* 86: 6077–6081, 1989), and purified transcription factors (Debs et al., *J. Biol. Chem.* 265: 10189–10192, 1990), in functional form. Cationic liposomes are readily available. For example, N[1-2,3-dioleyloxy)propyl]-N,N,N-triethyl-ammonium (DOTMA) liposomes are available under the trademark Lipofectin, from GIBCO BRL, Grand Island, N.Y. See also Felgner et al., *Proc. Natl. Acad. Sci. USA* 91: 5148–5152.87, 1994.

Other commercially available liposomes include Transfectace (DDAB/DOPE) and DOTAP/DOPE (Floerhinger). Other cationic liposomes can be prepared from readily available materials using techniques well known in the art. See, e.g., Szoka et al., *Proc. Natl. Acad. Sci. USA* 75: 4194–4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., METHODS OF IMMUNOLOGY (1983), Vol. 101, pp. 512–527; Szoka et al., *Proc. Natl. Acad. Sci. USA* 87: 3410–3414, 1990; Papahadjopoulos et al., *Biochim. Biophys. Acta* 394: 483, 1975; Wilson et al, *Cell* 17: 77, 1979; Deamer and Bangham, *Biochim. Biophys. Acta* 443: 629, 1976; Ostro et al., *Biochem. Biophys. Res. Commun.* 76: 836 , 1977; Fraley et al., *Proc. Natl. Acad. Sci. USA* 76: 3348, 1979; Enoch and Strittmatter, *Proc. Natl. Acad. Sci. USA* 76: 145, 1979; Fraley et al., *J. Biol. Chem.* 255: 10431, 1980; Szoka and Papahadjopoulos, *Proc. Natl. Acad. Sci. USA* 75: 145, 1979; and Schaefer-Ridderetal., *Science* 215: 166, 1982.

In addition, lipoproteins can be included with an IKKβ subgenomic polynucleotide for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

"Naked" IKKβ subgenomic polynucleotide molecules can also be used as gene delivery vehicles, as described in WO 90/11092 and U.S. Pat. No. 5,580,859. Such gene delivery vehicles can be either IKKβ DNA or RNA and, in certain embodiments, are linked to killed adenovirus. Curiel et al., *Hum. Gene. Ther.* 3: 147–154, 1992. Other suitable vehicles include DNA-ligand (Wu et al., *J. Biol. Chem.* 264: 16985–16987, 1989), lipid-DNA combinations (Felgner et al., *Proc. Natl. Acad. Sci. USA* 84: 7413 7417, 1989), liposomes (Wang et al., *Proc. Natl. Acad. Sci.* 84: 7851–7855, 1987) and microprojectiles (Williams et al., *Proc. Natl. Acad. Sci.* 88: 2726–2730, 1991).

The efficiency of naked IKKβ subgenomic polynucleotide uptake into cells can be increased by coating the polynucleotides onto biodegradable latex beads, which are efficiently transported and concentrated in the perinuclear region of the cells. IKKβ subgenomic polynucleotide-coated latex beads can be injected into cells and will be efficiently transported into cells after the beads initiate endocytosis, thus increasing gene transfer and expression efficiency. This method can be improved further by treating the beads to increase their hydrophobicity, thereby facilitating the disruption of the endosome and release of IKKβ subgenomic polynucleotides into the cytoplasm.

IKKβ expression can be decreased in a cell, for example to treat conditions in which decreased inflammatory response is desired. Reagents which specifically bind to an IKKβ expression product so as to decrease the level of functional IKKβ protein in a cell can be used for this purpose. In one embodiment of the invention, the reagent is a ribozyme, an RNA molecule with catalytic activity. See, e.g., Cech, *Science* 236: 1532–1539; 1987; Cech, *Ann. Rev. Biochem.* 59: 543–568; 1990, Cech, *Curr. Opin. Struct. Biol.* 2: 605–609; 1992, Couture and Stinchcomb, *Trends Genet.* 12: 510–515, 1996. Ribozymes can be used to inhibit gene function by cleaving an RNA sequence, as is known in the art (e.g., Haseloff et al., U.S. Pat. No. 5,641,673).

A coding sequence of an IKKβ gene can be used to generate ribozymes which will specifically bind to mRNA transcribed from the IKKβ gene. Methods of designing and constructing ribozymes which can cleave other RNA molecules in trans in a highly sequence specific manner have been developed and described in the art (see Haseloff et al. *Nature* 334: 585–591, 1988). For example, the cleavage activity of ribozymes can be targeted to specific IKKβ RNAs by engineering a discrete "hybridization" region into the ribozyme. The hybridization region contains a sequence complementary to the target IKKβ RNA and thus specifically hybridizes with the target (see, for example, Gerlach et al., EP 321,201). The nucleotide sequences shown in SEQ ID NOS:1, 2, and 3 provide sources of suitable hybridization region sequences. Longer complementary sequences can be used to increase the affinity of the hybridization sequence for the target. The hybridizing and cleavage regions of the IKKβ ribozyme can be integrally related; thus, upon hybridizing to the target IKKβ RNA through the complementary regions, the catalytic region of the ribozyme can cleave the target.

IKKβ ribozymes can be introduced into cells as part of a construct, as is known in the art and described above. Mechanical methods, such as microinjection, liposome-mediated transfection, electroporation, or calcium phosphate precipitation, can be used to introduce the ribozyme-containing construct into cells in which it is desired to decrease IKKβ expression, as described above. Alternatively, if it is desired that the cells stably retain the construct, it can be supplied on a plasmid and maintained as a separate element or integrated into the genome of the cells, as is known in the art. The construct can include transcriptional regulatory elements, such as a promoter element, an enhancer or UAS element, and a transcriptional terminator signal, for controlling transcription of IKKβ ribozymes in the cells.

In another embodiment of the invention, the level of IKKβ protein is decreased using an antisense oligonucleotide sequence. The antisense sequence is complementary to at last a portion of a sequence encoding IKKβ selected from the nucleotide sequences shown in SEQ ID NOS:1, 2, and 3. Preferably, the antisense oligonucleotide sequence is at least 11 nucleotides in length, but can be at least 12, 15, 20, 25, 30, 35, 40, 45, or 50 or more nucleotides long. Longer sequences can also be used. IKKβ antisense oligonucleotide molecules can be provided in a construct and introduced into cells as disclosed herein to decrease the level of functional IKKβ protein in the cells.

IKKβ antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phzsphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20: 1–8, 1994; Sonveaux, *Meth. Mol. Biol.* 26: 1–72, 1994; Uhlmann et al., *Chem. Rev.* 90: 543–583, 1990.

Precise complementary is not required for successful duplex formation between an antisense molecule and the complementary coding sequence of an IKKβ gene. Antisense molecules which comprise, for example, 2, 3, 4, or 5 or more stretches of contiguous nucleotides which are precisely complementary to an IKKβ coding sequence, each separated by a stretch of contiguous nucleotides which are not complementary to adjacent IKKβ coding sequences, can provide targeting specificity for IKKβ mRNA. Preferably, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular IKKβ coding sequence.

IKKβ antisense oligonucleotides can be modified without affecting their ability to hybridize to an IKKβ coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, can also be employed in a modified antisense oligonucleotide. These modified oligonucleotides can be prepared by methods well known in the art. See, e.g., Agrawal et al., *Trends Biotechnol.* 10: 152–158, 1992; Uhlmann et al., *Chem. Rev.* 90: 543–584, 1990; Uhlmann et al., *Tetrahedron. Lett.* 215: 3539–3542, 1987.

Antibodies of the invention which specifically bind to IKKβ epitopes, particularly to the IκB-binding domain of IKKβ, can also be used to alter levels of functional IKKβ protein, by binding to IKKβ protein and decreasing the level of IKKβ protein which can function in the cell. Polynucleotides encoding single-chain antibodies of the invention can be introduced into cells as described above.

To increase IKKβ gene expression, all or a portion of an IKKβ gene or expression product can be introduced into a cell. Optionally, the gene or expression product can be a component of a therapeutic composition comprising a pharmaceutically acceptable carrier (see below). The entire IKKβ coding sequence can be introduced, as described above. Alternatively, a portion of the IKKβ protein which is capable of phosphorylating a JNK substrate can be identified and that portion or a nucleotide sequence encoding it can be introduced into the cell. Portions of IKKβ protein which phosphorylate JNK can be identified by introducing expression constructs which express different portions of the protein into cells and assaying IKKβ kinase activity, as described above.

Compositions comprising IKKβ antibodies, ribozymes, or antisense oligonucleotides can optionally comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in IKKβ compositions, for example, mineral salts such as hydrochlorides, hydrobromides, phosphates, or sulfates, as well as salts of organic acids such as acetates, propionates, malonates, or benzoates. IKKβ compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for an IKKβ composition.

Typically, an IKKβ composition is prepared as an injectable, either as a liquid solution or suspension; however, solid forms suitable for solution or suspension in liquid vehicles prior to injection can also be prepared. An IKKβ composition can also be formulated into an enteric coated tablet or gel capsule according to known methods in the art, such as those described in U.S. Pat. No. 4,853,230, EP 225,189, AU 9,224,296, and AU 9,230,801.

Administration of IKKβ compositions of the invention can include local or systemic administration, including injection, oral administration, particle gun, or catheterized administration, and topical administration. Various methods can be used to administer an IKKβ composition directly to a specific site in the body.

Receptor-mediated targeted delivery can be used to deliver therapeutic compositions containing IKKβ subgenomic polynucleotides, proteins, or reagents such as antibodies, ribozymes, or antisense oligonucleotides to specific tissues. Receptor-mediated delivery techniques are described in, for example, Findeis et al. (1993), *Trends in Biotechnol.* 11, 202–05; Chiou et al. (1994), GENE THERAPEUTICS: METHODS AND APPLICATIONS OF DIRECT GENE TRANSFER (J. A. Wolff, ed.); Wu & Wu (1988), *J. Biol. Chem.* 263, 621–24; Wu et al. (1994), *J. Biol. Chem.* 269, 542–46; Zenke et al. (1990), *Proc. Natl. Acad. Sci. U.S.A.* 87, 3655–59; Wu et al. (1991), *J. Biol. Chem.* 266, 338–42.

Expression of an endogenous IKKβ gene in a cell can also be altered by introducing in frame with the endogenous IKKβ gene a DNA construct comprising an IKKβ targeting sequence, a regulatory sequence, an exon, and an unpaired splice donor site by homologous recombination, such that a homologously recombinant cell comprising the DNA construct is formed. The new transcription unit can be used to turn the IKKβ gene on or off as desired. This method of affecting endogenous gene expression is taught in U.S. Pat. No. 5,641,670.

The targeting sequence is a segment of at least 10, 12, 15, 20, or 50 contiguous nucleotides selected from the nucleotide sequences shown in SEQ ID NOS:1, 2, or 3. The transcription unit is located upstream of a coding sequence of the endogenous IKKβ gene. The exogenous regulatory sequence directs transcription of the coding sequence of the IKKβ gene.

Both the dose of an IKKβ composition and the means of administration can be determined based on the specific qualities of the therapeutic composition, the condition, age, and weight of the patient, the progression of the disease, and other relevant factors. Preferably, a therapeutic composition of the invention increases or decreases expression of the IKKβ gene by 50%, 60%, 70%, or 80%. Most preferably, expression of the IKKβ gene is increased or decreased by 90%, 95%, 99%, or 100%. The effectiveness of the mechanism chosen to alter expression of the IKKβ gene can be assessed using methods well known in the art, such as hybridization of nucleotide probes to mRNA of the IKKβ gene, quantitative RT-PCR, or detection of an IKKβ protein using specific antibodies of the invention.

If the composition contains IKKβ protein, polypeptide, or antibody, effective dosages of the composition are in the range of about 5 μg to about 50 μg/kg of patient body weight, about 50 μg to about 5 mg/kg, about 100 μg to about 500 μg/kg of patient body weight, and about 200 to about 250 μg/kg.

Therapeutic compositions containing IKKβ subgenomic polynucleotides can be administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action and efficacy of transformation and expression are considerations that will effect the dosage required for ultimate efficacy of the IKKβ subgenomic polynucleotides. Where greater expression is desired over a larger area of tissue, larger amounts of IKKβ subgenomic polynucleotides or the same amounts can be readministered in a successive protocol of administrations or in several administrations to different adjacent or close tissue to effect a positive therapeutic outcome. In all cases, routine experimentation in clinical trials will determine specific ranges for optimal therapeutic effect.

The invention also provides a method to identify test compounds which modulate a pro-inflammatory response. A test compound can be a pharmacologic agent already known in the art or can be a compound previously unknown to have any pharmacological activity. The compound can be naturally occurring or designed in the laboratory. It can be isolated from microorganisms, animals, or plants, and can be produced recombinantly, or synthesized by chemical methods known in the art.

Such test compounds can be identified by their effect, for example, on the phosphorylation activiity of IKKβ or on IKKβ synthesis or binding to IκB. Phosphorylation activity of IKKβ, IKKβ synthesis, or IKKβ binding to IκB in the presence or absence of a test compound can be measured in a biological sample. The biological sample can be whole cells or extracts of human cells which express IKKβ, such as heart, brain, lung, liver, muscle, kidney, or testis, or in whole cells or extracts of human cell lines. A variety of cell lines are commercially available or can be obtained from the ATCC for this purpose.

The effect of a test compound on IKKβ synthesis can also be used to identify test compounds which modulate pro-inflammatory responses. Synthesis of IKKβ can be measured by any means for measuring protein synthesis known in the art, such as incorporation of labeled amino acids into proteins and detection of labeled IKKβ protein in a polyacrylamide gel. The amount of IKKβ protein can be detected, for example, using IKKβ-specific antibodies of the invention in Western blots. The amount of IKKβ protein synthesized in the presence or absence of a test compound can be determined by ;my means known in the art, such as comparison of the amount of IKKβ synthesized With the amount of IKKβ protein present in a standard curve.

The effect of a test compound on IKKβ synthesis can also be measured by Northern blot analysis, by measuring the amount of IKKβ mRNA expression in response to the test compound using IKKβ specific nucleotide probes of the invention, as is known in the art.

IKKβ activity can be measured using in vitro kinase assays, as described in WO 96/36642. For identifying a test substance which modulates IKKβ activity, a kinase assay can be carried out using an IKKβ substrate, and a radioactive marker such as [γ-32$^P$]ATP. The substrate can be, for example, IκB.

Typically, the biological sample is contacted with a range of concentrations of the test compound, such as 1.0 nM, 5.0 nM, 10 nM, 50 nM, 100 nM, 500 nM, 1 mM, 10 mM, 50 mM, and 100 mM. Preferably, the test compound increases or decreases phosphorylation of IKKβ, IKKβ synthesis, or IKKβ binding to IκB by 60%, 75%, or 80%. More preferably, an increase or decrease of 85%, 90%, 95%, or 98% is achieved. A test compound which increases IKKβ phosphorylation activity, synthesis, or binding to IκB is a potential drug for inhibiting an inflammatory response. A test compound which decreases IKKβ phosphorylation activity, synthesis, or binding to IκB is a potential drug for enhancing an inflammatory response.

The complete contents of all references cited in this disclosure are incorporated herein by reference.

We claim:

1. A cDNA molecule which encodes a protein having an amino acid sequence which is at least 85% identical to an amino acid sequence encoded by a nucleotide sequence selected from the group consisting of SEQ ID NOS:2 and 3, wherein percent identity is determined using a Smith-Waterman homology search algorithm using an affine gap search with a gap open penalty of 12 and a gap extension penalty of 1.

2. The cDNA molecule of claim 1 which comprises a nucleotide sequence as shown in SEQ ID NO:2.

3. The cDNA molecule of claim 1 which comprises a nucleotide sequence as shown in SEQ ID NO:3.

4. A cDNA molecule which is at least 85% identical to a nucleotide sequence selected from the group consisting of SEQ ID NOS:2 and 3, wherein percent identity is determined using a Smith-Waterman homology search algorithm using an affine gap search with a gap open penalty of 12 and a gap extension penalty of 1.

5. An isolated and purified subgenomic polynucleotide comprising a nucleotide sequence which hybridizes to a nucleotide sequence selected from the group consisting of SEQ ID NOS:2 and 3 after washing with 0.2×SSC at 65° C.

6. A construct comprising:
a promoter; and
a polynucleotide segment comprising a nucleotide sequence selected from the group consisting of at least 1000 contiguous nucleotides of SEQ ID NO:2 and at least 750 contiguous nucleotides of SEQ ID NO:3, wherein the polynucleotide segment is located downstream from the promoter, wherein transcription of the polynucleotide segment initiates at the promoter.

7. The construct of claim 6 which has the nucleotide sequence of SEQ ID NO:2.

8. The construct of claim 6 which has the nucleotide sequence of SEQ ID NO:3.

9. A host cell comprising a construct which comprises:
a promoter; and
a polynucleotide segment comprising a nucleotide sequence selected from the group consisting of at least 1000 contiguous nucleotides of SEQ ID NO:2 and at least 750 contiguous nucleotides of SEQ ID NO:3.

10. The host cell of claim 9 which has the nucleotide sequence of SEQ ID NO:2.

11. The host cell of claim 9 which has the nucleotide sequence of SEQ ID NO:3.

12. An isolated and purified subgenomic polynucleotide comprising at least 1000 contiguous nucleotides of SEQ ID NO:2 or its complement.

13. The isolated and purified subgenomic polynucleotide of claim 12 which comprises the nucleotide sequence of SEQ ID NO:2.

14. An isolated and purified subgenomic polynucleotide comprising at least 750 contiguous nucleotides of SEQ ID NO:3 or its complement.

15. The isolated and purified subgenomic polynucleotide of claim 14 which comprises the nucleotide sequence of SEQ ID, NO:3.

* * * * *